(12) United States Patent
Woodall et al.

(10) Patent No.: US 6,561,023 B2
(45) Date of Patent: May 13, 2003

(54) CELLULOSE-BASED WATER SENSING ACTUATOR

(75) Inventors: Robert Woodall, Panama City Beach, FL (US); Felipe Garcia, Panama City, FL (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 15 days.

(21) Appl. No.: 09/839,841

(22) Filed: Apr. 23, 2001

(65) Prior Publication Data

US 2002/0178811 A1 Dec. 5, 2002

(51) Int. Cl.$^7$ ............................................... G01N 19/00
(52) U.S. Cl. ................................................. 73/335.06
(58) Field of Search ........................... 73/29.01, 29.05, 73/73, 335, 335.06

(56) References Cited

U.S. PATENT DOCUMENTS

| | | | | |
|---|---|---|---|---|
| 5,853,246 A | * | 12/1998 | Lowder | 374/109 |
| 6,038,922 A | * | 3/2000 | Mauze et al. | 73/335.08 |
| 6,182,507 B1 | * | 2/2001 | Sanford et al. | 73/335.06 |
| 6,202,480 B1 | * | 3/2001 | Mauze et al. | 73/77 |
| 6,276,196 B2 | * | 8/2001 | Mauze et al. | 73/64.45 |

* cited by examiner

*Primary Examiner*—Hezron Williams
*Assistant Examiner*—Marissa Ferguson
(74) *Attorney, Agent, or Firm*—Harvey A. Gilbert; Donald G. Peck

(57) ABSTRACT

An integrated water sensing actuator is based on a fibrous cellulosic material having anisotropic moisture-absorbing properties such that it's dried-in strain is greatest along one axis thereof. A plug of the dry and compressed fibrous cellulosic material has a powder material coated thereon and mixed therewith. The plug is compressed along it's axis of greatest dried-in strain and is fitted in a water-permeable housing adjacent a piston. The powder material is inert with respect to the cellulosic material and initiates a chemical reaction when exposed to water such that a product of the chemical reaction is water. Immersion of the housing in water causes expansion of the plug and corresponding movement of the piston.

14 Claims, 2 Drawing Sheets

CELLULOSE-BASED WATER SENSING ACTUATOR

CROSS-REFERENCE TO RELATED PATENT APPLICATIONS

This patent application is co-pending with two related patent applications entitled "SAFETY AND ARMING DEVICE USING CELLULOSE-BASED SENSOR/ACTUATOR" (Navy Case No. 82769) and "MOISTURE-ABSORBING CELLULOSE-BASED MATERIAL" (Navy Case No. 82772), filed on the same date by the same inventors as this patent application.

ORIGIN OF THE INVENTION

The invention described herein was made in the performance of official duties by employees of the Department of the Navy and may be manufactured, used, licensed by or for the Government for any governmental purpose without payment of any royalties thereon.

FIELD OF THE INVENTION

The invention relates generally to water sensors and actuators, and more particularly to an integrated water sensing actuator using a cellulose-based moisture absorbing material.

BACKGROUND OF THE INVENTION

Some military explosive systems used in maritime environments are required to first sense the presence of water and then, only after water is sensed, actuate the elements of a device's operational safety and reliability sequence. For example, a fuze on an air-launched projectile/weapon intended to operate under water typically uses a sensor to sense the presence of water and an actuator to initiate an arming sequence. Usually, the sensing and actuation functions are achieved by two separate devices within the fuze where actuation of critical logic gates (e.g., mechanical, electrical or chemical gates) depends on a signal from the water sensing portion of the fuze. Since standards governing premature actuation (i.e., prior to water being sensed) generally dictate a failure rate of less than one failure in a million, it is imperative that the two separate devices perform reliably both individually and in combination with one another. However, such coordinated operation typically utilizes a complex and expensive mechanism that is inherently prone to failure owing to its complexity.

In an attempt to simplify the sensing/actuation problem, the water sensing and actuation functions could be integrated with one another. U.S. Pat. No. 6,182,507 describes one such prior art integrated mechanical water sensor in which compressed cotton balls are constrained in an open frame as a means to provide for water absorption and subsequent cotton expansion where the force of expansion is used to move a piston. However, compressed cotton balls do not provide a reliable means of moisture absorption in harsh underwater environments and, therefore, are not reliable as a means of producing work when subjected to immersion in such environments. This is because the compressed cotton balls rely on surface absorption of moisture for its expansion. However, high-levels of naturally-occurring impurities and man-made pollutants often found in underwater environments can cover the surface area of the cotton thereby impeding the absorption of water.

SUMMARY OF THE INVENTION

Accordingly, it is an object of the present invention to provide a water sensing actuator that can function in moisture environments having impurities and pollutants.

Another object of the present invention is to provide a water sensing actuator that integrates it's sensing and actuating functions with a single structure.

Still another object of the present invention is to provide an integrated water sensing actuator that functions reliably in harsh underwater environments.

Other objects and advantages of the present invention will become more obvious hereinafter in the specification and drawings.

In accordance with the present invention, an integrated water sensing actuator is based on a fibrous cellulosic material having anisotropic moisture-absorbing properties such that dried-in strain of the cellulosic material is greatest along one axis thereof. In the invention, a plug of the dry and compressed fibrous cellulosic material has a powder material coated thereon and mixed therewith. The plug is compressed along its axis of greatest dried-in strain and is fitted in a portion of a water-permeable housing adjacent one end thereof. The powder material is inert with respect to the cellulosic material and initiates a chemical reaction when exposed to water such that a product of the chemical reaction is water. A piston is fitted in the housing adjacent the plug. Immersion of the housing in water causes expansion of the plug and corresponding movement of the piston.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

Figure 1:
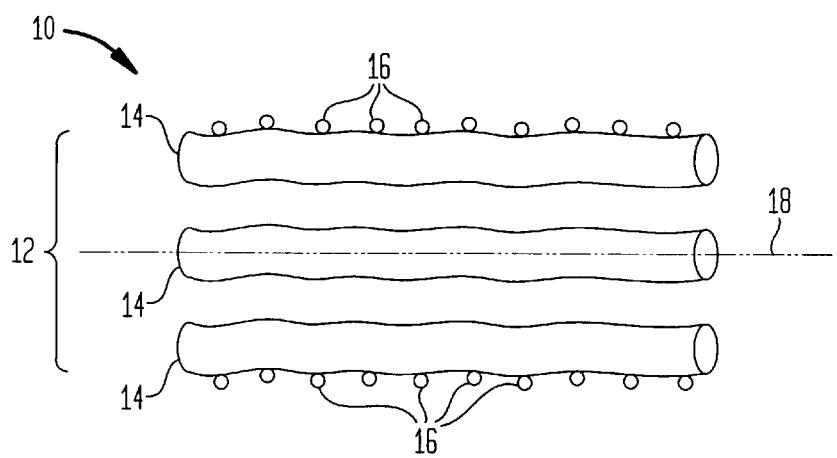
FIG. 1 is a schematic diagram of a chemically-enhanced moisture-absorbing material.

Referring now to the drawings, and more particularly to FIG. 1, a chemically-enhanced moisture-absorbing material is shown and referenced generally by numeral 10. Moisture-absorbing material 10 is depicted as a microscopic abstraction useful for illustrating the mechanisms used by the present invention.

Moisture-absorbing material 10 is shown in its dry state, i.e., prior to its exposure to a fluid environment such as water. In this state, material 10 is defined by a fibrous cellulosic material consisting of a collection 12 of fibrous tubes 14 with powder particles 16 of a water-reactive material coating or adhering to those portions of tubes 14 defining the exterior surface of material 10.

In general, the fibrous cellulosic material represented by tubes 14 is preferably derived from any plant-based cellulose material that has been processed to exhibit anisotropic behavior/properties in terms of its moisture-absorbing capabilities. More specifically, the fibrous cellulosic material represented by tubes 14 is processed such that the dried-in strain thereof is greatest along an axis 18 of material 10. A variety of processing techniques can be used to achieve this state for fibers 14. Such processing generally includes several of the following processes:

Cleaning foreign matter (e.g., seeds) from the cellulosic material

Water washing the cellulosic material

Surface treating the cellulosic material by means of nitration, bleaching, etc.

Raking or aligning the fibers in the cellulosic material

Stretching the fibers of the cellulosic material along an axis thereof that exhibits the greatest dried-in strain Drying the cellulosic material The particular processes and their order can vary depending on the type of cellulosic material, the desired absorption properties, etc., and are therefore not a limitation of the present invention.

As mentioned above, it is preferable that the cellulosic material in the present invention be derived from plants as they are inexpensive, renewable and environmentally safe. The approximate cellulose content for a variety of plant-derived cellulose materials is listed below.

| Material | Percent Cellulose |
| --- | --- |
| Cotton | 98% |
| Ramie | 86 |
| Hemp | 65 |
| Jute | 58 |
| Deciduous woods | 41–42 |
| Coniferous woods | 41–44 |
| Cornstalks | 43 |
| Wheat straw | 42 |

The greater the percentage of cellulose, the greater the absorption capability. Therefore, the most absorbent type of material 10 will utilize cotton cellulose-based tubes 14.

Figure 2A:
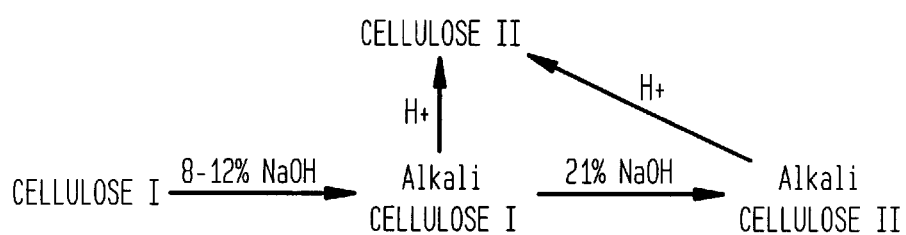
FIG. 2A is a schematic chemical diagram of one method of converting a cellulose material's naturally-occurring Cellulose I form to the Cellulose II form utilized by the present invention.
Figure 2B:
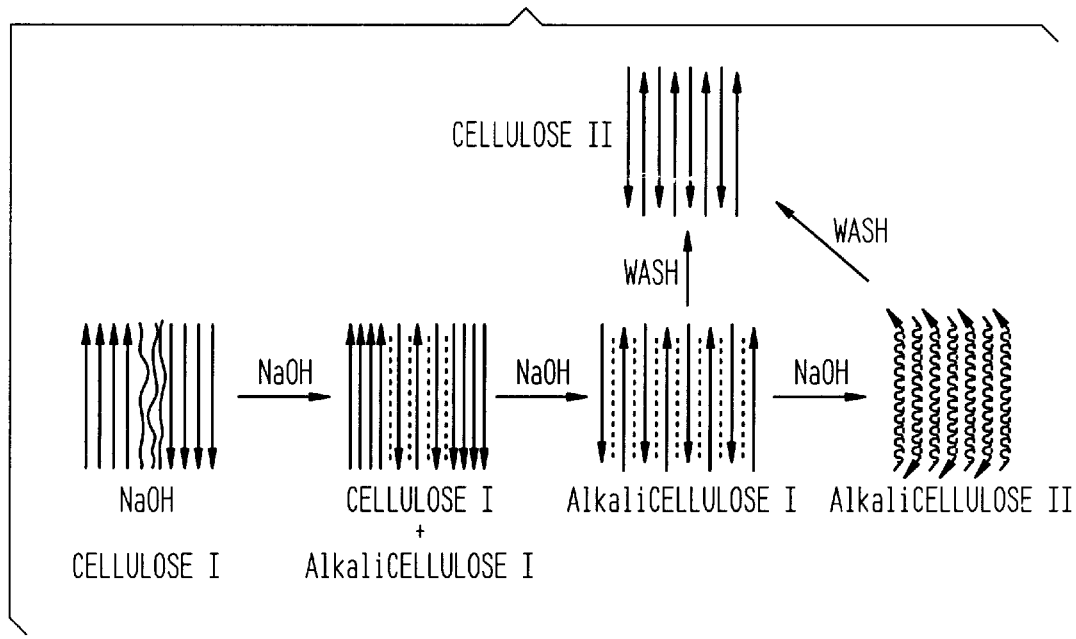
FIG. 2B is a schematic diagram illustrating the conversion of the Cellulose I form to the Cellulose II form utilized by the present invention.

The state of the dry cellulosic material used in the present invention can also be defined by the form known as Cellulose II. The Cellulose II form is converted or refined from the native form of a cellulose material or Cellulose I. A well known example of Cellulose I to Cellulose II conversion processing is depicted chemically in FIG. 2A and graphically in FIG. 2B. Note that the parallel arrows in the Cellulose II state are indicative of aligned fibrous cellulose tubes such as tubes 14 described above. For further details of cellulose refinement processing, a number of prior art references can be consulted. For example, see "Chemistry of Pulp and Paper Making," by Edwin Sutermeister, 3rd edition, Wiley Publishing, New York, 1941, or see "Cellulose Chemistry," by Mark Plungerian, Chemical Publishing Company, Brooklyn, N.Y., 1943.

The material selected for powder particles 16 should be inert with respect to the cellulosic material and reactive with respect to the moisture (e.g., water) to be absorbed. Preferably, the material selected for powder particles 16 should also generate water as a product of its chemical reaction with water. For example, if powder particles 16 comprise a mixture of sodium bicarbonate ($NaHCO_3$) and citric acid ($H_3C_6H_5O_7$), a reaction of this mixture with water yields sodium citrate ($Na_3C_6H_5O_7$), carbon dioxide ($CO_2$) and water ($H_2O$). Another preferred example for powder particles 16 is a mixture of sodium bicarbonate ($NaHCO_3$) and potassium hydrogen tartrate ($KHC_4H_4O_6$). A reaction of this mixture with water yields potassium sodium tartrate ($KNaC_4H_4O_6$), carbon dioxide and water. Note that any amount of water is sufficient to start the reaction. Once started, no additional water is needed as the reaction self-produces water.

Upon immersion in water, powder particles 16 solvate with the heat of salvation being released/absorbed from the surroundings to increase or decrease the localized temperature of the reaction zone on the surface of material 10. This localized temperature gradient induces a corresponding mass transfer increase between the hot and cold regions as they pursue thermal equilibrium. The thermal effect increases the mass transfer effect of adsorption at the surface of the cellulose fiber that is in contact with water, i.e., this thermal effect increases the mass transfer effect of adsorption at the boundary that separates the wet versus dry portion of material 10. If powder particles 16 also generate more water when chemically reacting with water, the additional water increases turbulence and changes concentration gradients which, in turn, increase the mass transfer effect of absorption at the surface of material 10.

Figure 3:
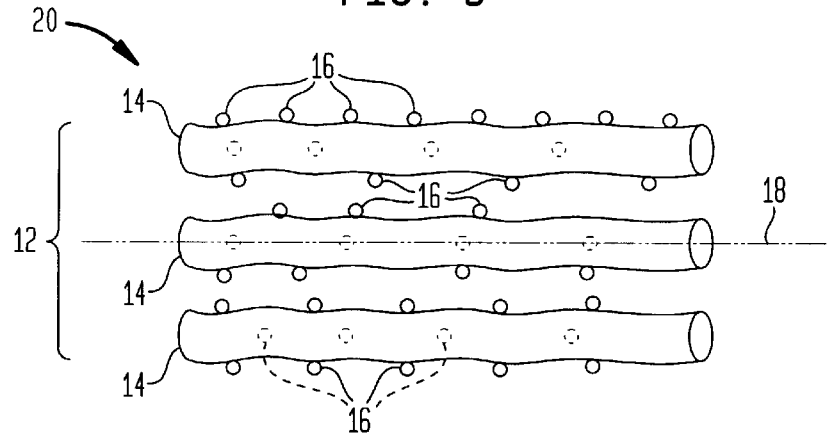
FIG. 3 is a schematic diagram of another chemically-enhanced moisture-absorbing material.

Another embodiment of a chemically-enhanced moisture-absorbing material is illustrated schematically in FIG. 3 and is referenced generally by numeral 20. Similar to material 10, material 20 includes a fibrous cellulosic material represented by a collection 12 of tubes 14. Powder particles 16 are coated/adhered to the portions of tubes 14 defining the exterior surface of material 20. In addition, powder particles 16 are mixed with tubes 14 to reside therebetween and, in some cases, within tubes 14 as represented by dotted line versions of particles 16. To achieve such a mixed structure, the size of powder particles 16 must be less than (e.g., 10 percent smaller) the porosity of the structure defined by tubes 14. The mixing of powder particles 16 with tubes 14 can be achieved by tumbling the cellulosic material with powder particles 16. Such tumbling processes are standard and well known within the art of cellulose processing.

When immersed in water, adsorption and absorption effects at the surface of material 20 will be the same as material 10. However, the presence of powder particles 16 between and in tubes 14 provides an additional mass transfer effect that increases water adsorption and absorption. In addition, if one of the above-described sodium bicarbonate mixtures is used for powder particles 16, the generation of gaseous carbon dioxide not only improves adsorption and absorption, but also introduces the mass transfer effect of diffusion through material 20.

Figure 4:
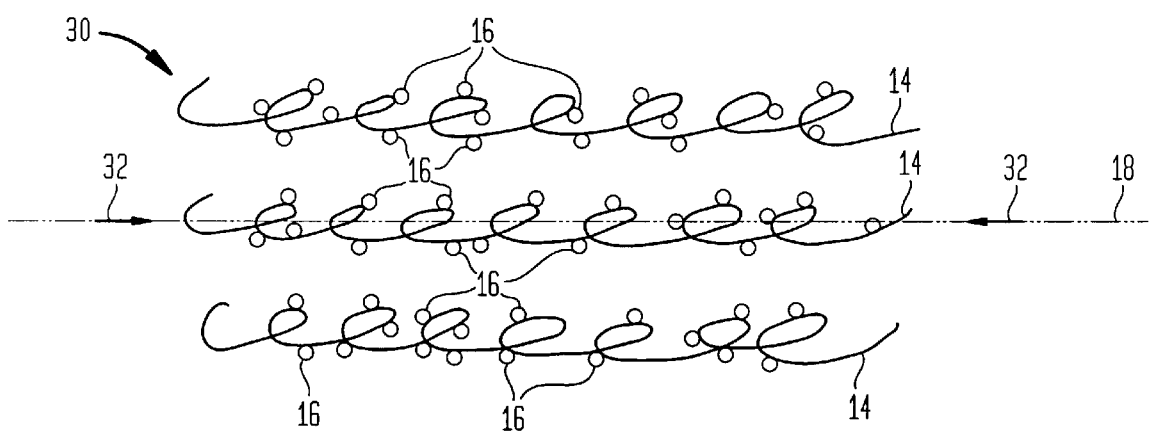
FIG. 4 is a schematic diagram of a moisture-absorbing, work-producing material structure used in the present invention.

While each of materials 10 and 20 is useful for pure moisture-absorbing applications, the present invention utilizes a moisture-absorbing, work-producing structure. Such a structure is illustrated schematically in FIG. 4 and is referenced generally by numeral 30 where structure 30 uses material 20 as its basis.

Structure 30 is similar to material 20 in that it includes tubes 14 of a cellulosic material coated and mixed with powder particles 16. However, structure 30 has further been compressed along axis 18 (as indicated by arrows 32) which is the axis of greatest dried-in strain or the axis of polymer chain alignment in the case of the Cellulose II form. Accordingly, tubes 14 are illustrated in a "corkscrew" fashion to indicate that they are in a state of compression. However, it is to be understood that compression of tubes 14 is carried out at pressures/forces such that the dried-in strain of tubes 14 along axis 18 is not damaged. That is, compressed tubes 14 can be considered to remain substantially aligned with axis 18.

When structure 30 in its dry state is immersed in water, the above-described mass transfer effects applicable to material 20 also apply to structure 30. However, structure 30 is specifically designed to provide work along axis 18 as the absorption, absorption and diffusion mass transfer effects will cause structure 30 to expand along axis 18. By coating/mixing tubes 14 with powder particles 16 that chemically react with water to produce water, expansion of structure 30 along axis 18 will take place even if there are impurities in the water of activation. Diffusion of the chemically-produced water through structure 30 can be enhanced if a gaseous product such as carbon dioxide is also produced by the chemical reaction. Thus, structure 30 is capable of being used as a reliable water sensing, work-producing element in harsh (i.e, impure and/or polluted) underwater environments.

Figure 5:
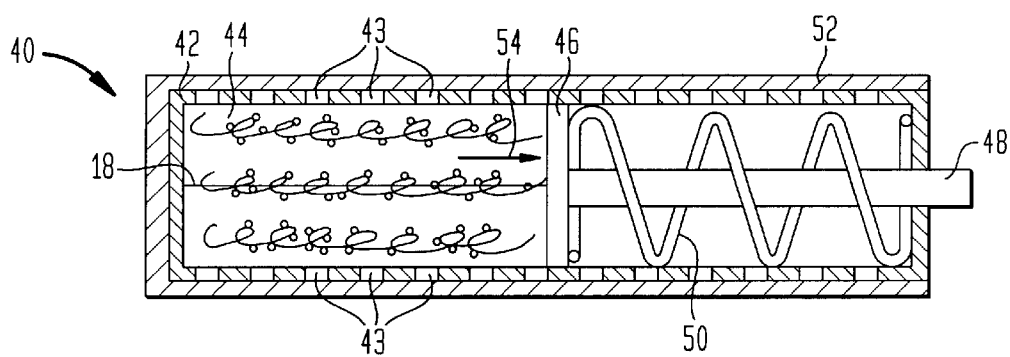
FIG. 5 is a cross-sectional view of an integrated water sensing actuator in accordance with the present invention.

Referring now to FIG. 5, an integrated water sensing actuator in accordance with the present invention is shown and referenced generally by numeral 40. Actuator 40 has a water permeable housing 42 which can be a made from a rigid material having holes 43 formed therearound. Housing 42 could also be realized by a rigid permeable membrane type of material. Fitted in one end of housing 42 is a plug 44 of a moisture-absorbing, work-producing material structure that is preferably structure 30 described above. That is, plug 44 is in its dry and compressed state prior to being exposed to water. Plug 44 is positioned in housing 42 such that its axis of greatest dried-in strain (i.e., axis 18) is aligned approximately perpendicular to a piston 46 that is fitted in housing 42 adjacent plug 44. A piston rod 48 extending from and through housing 42 can be coupled to piston 46. Piston 46 can be retained against plug 44 by means of, for example, a light spring 50 that cooperates with housing 42 and piston 46. The bias force of spring 50 should be sufficient to retain plug 44 in position prior to immersion in water, yet small enough to be overcome by the expansion of plug 44 as will be explained below. Finally, a water-impenetrable and removable safety cover 52 can encase housing 42 prior to its use to prevent premature expansion of plug 44.

In use, safety cover 52 is removed prior to actuator 40 coming into contact with (or being immersed in) water. Once actuator 40 is exposed to water, any amount of water entering housing 42 will initiate the above-described chemical reaction. Resulting expansion of plug 44 will occur in the direction of axis 18 in accordance with the adsorption, absorption and diffusion mechanisms described above with respect to structure 30. The resulting expansion of plug 44 applies a force 54 on piston 46 causing it to move along with piston rod 48 to the right in FIG. 5. As mentioned above, the bias force of spring 50 will be less than that of force 54. However, spring 50 should maintain piston 46 in constant engagement with plug 44 during the expansion of plug 44 to insure a smooth transfer of force 54. Thus, the movement of piston rod 48 serves as the actuator movement for a device/system 100 coupled to piston rod 48. The particular device/system 100 is not part of the present invention and is, therefore, not a limitation on the present invention.

The advantages of the present invention are numerous. A simple integrated water sensing actuator is made from inexpensive/renewable cellulose materials and harmless chemicals. The compressed chemically-enhanced cellulose-based material structure provides a work-producing structure that will function reliably even in impure, polluted or harsh water environments as only a trace amount of water is needed to generate the work force.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A water sensing actuator comprising:
    a water permeable housing;
    a fibrous cellulosic material having fibers extending therealong, said cellulosic material having a dried-in strain that is greatest along an axis of said cellulosic material;
    a powder material adhered to and residing between said fibers, said powder material being inert with respect to said cellulosic material and initiating a chemical reaction when exposed to water, wherein a product of said chemical reaction is water;
    said cellulosic material, with said powder material adhered to and residing between said fibers thereof, being compressed along said axis of said cellulosic material to form a plug having an axis of compression that is aligned with said axis of said cellulosic material, said plug being fitted in a portion of said housing adjacent one end thereof; and
    a piston fitted in said housing adjacent said plug and approximately perpendicular to said axis of compression, wherein immersion of said housing in water causes expansion of said plug along said axis of compression and corresponding movement of said piston.

2. A water sensing actuator as in claim 1 wherein said cellulosic material is derived from a plant.

3. A water sensing actuator as in claim 1 wherein said cellulosic material is cotton cellulose.

4. A water sensing actuator as in claim 1 wherein said powder material is selected from the group consisting of: a mixture of sodium bicarbonate and citric acid; and a mixture of sodium bicarbonate and potassium hydrogen tartrate.

5. A water sensing actuator as in claim 1 further comprising means for retaining said piston adjacent said plug before and during said expansion thereof.

6. A water sensing actuator as in claim 5 wherein said means comprises a spring fitted in said housing.

7. A water sensing actuator as in claim 1 wherein said powder material is selected such that another product of said chemical reaction is gaseous.

8. A water sensing actuator comprising:
    a water permeable housing;
    a fibrous cellulosic material defined by a Cellulose II form having fibrous cellulose tubes substantially aligned with one another to define an axis of said cellulosic material;
    a powder material adhered to and residing between and in said cellulose tubes, said powder material being inert with respect to said cellulosic material and initiating a chemical reaction when exposed to water, wherein a product of said chemical reaction is water;
    said cellulosic material, with said powder material adhered to and residing between and in said cellulose tubes thereof, being compressed along said axis to form said plug having an axis of compression that is aligned with said axis of said cellulosic material, said plug being fitted in a portion of said housing adjacent one end thereof; and a piston fitted in said housing adjacent said plug and approximately perpendicular to said axis of compression, wherein immersion of said housing in water causes expansion of said plug along said axis of compression and corresponding movement of said piston.

9. A water sensing actuator as in claim 8 wherein said cellulosic material is derived from a plant.

10. A water sensing actuator as in claim 8 wherein said cellulosic material is cotton cellulose.

11. A water sensing actuator as in claim 8 wherein said powder material is selected from the group consisting of: a mixture of sodium bicarbonate and citric acid; and a mixture of sodium bicarbonate and potassium hydrogen tartrate.

12. A water sensing actuator as in claim 8 further comprising means for retaining said piston adjacent said plug before and during said expansion thereof.

13. A water sensing actuator as in claim 12 wherein said means comprises a spring fitted in said housing.

14. A water sensing actuator as in claim 8 wherein said powder material is selected such that another product of said chemical reaction is gaseous.

* * * * *